US00PP13503P2

(12) United States Plant Patent
Zaiger et al.

(10) Patent No.: US PP13,503 P2
(45) Date of Patent: Jan. 21, 2003

(54) INTERSPECIFIC TREE NAMED 'SPICEZEE'

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 10/038,465

(22) Filed: Jan. 7, 2002

(51) Int. Cl.[7] ..... A01H 5/00
(52) U.S. Cl. ..... Plt./180
(58) Field of Search ..... Plt./180

*Primary Examiner*—Bruce R. Campell
*Assistant Examiner*—Anne Marie Grünberg

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consists of the following combination of desirable features:

1. Vigorous, upright growth of the tree.
2. Fruit with excellent flavor and eating quality.
3. Fruit with unique maroon-red skin color.
4. Heavy and regular production of fruit.
5. Unique maroon-red growth of the new leaves.

1 Drawing Sheet

STATEMENT REGARDING FEDERALLY SPONSORED RESEARCH OR DEVELOPMENT

Not applicable.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of peach, nectarine and plum trees, which are known to us, and mentioned herein, 'Royal Gold' Peach (U.S. Plant Pat. No. 2663), 'May Grand' Nectarine (U.S. Plant Pat. No. 2,794), 'Early Sungrand' Nectarine (U.S. Plant Pat. No. 1,420) and 'Red Beaut' Plum (U.S. Plant Pat. No. 2,539).

ORIGIN OF THE VARIETY

The new and distinct variety of interspecific tree [(*Prunus persica* var. *nucipersica*×(*Prunus persica* var. *nucipersica*×*Prunus persica*))×(*Prunus persica* var. *nucipersica*×(*Prunus salicina*×*Prunus persical*))] was developed by us in experimental orchard as an open pollinated seedling from seed collected from a cross between proprietary lines of immediate parents with field identification numbers 10LA512 and 41GF72. The maternal parent (10LA512) originated form a cross between a seedling from 'May Grand' Nectarine (U.S. Plant Pat. No. 2,794) crossed with a seedling from a cross of 'Early Sungrand' Nectarine (U.S. Plant Pat. No. 1,420) and 'Royal Gold' Peach (U.S. Plant Pat. No. 2,663). The paternal parent (41GF72) originated from an open pollinated seedling selection that was developed from a nectarine of unknown parentage crossed with a seedling that originated from 'Red Beaut' Plum (U.S. Plant Pat. No. 2,539) crossed with a peach of unknown parentage. A large number of these open pollinated seedlings were planted and grown on their own root system, during which time we recognized the potential of the desirable fruit characteristics and selected the present variety in 1996 for asexual reproduction and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new interspecific tree [(*Prunus persica* var. *nucipersica*×(*Prunus persica* var. *nucipersica*×*Prunus persica*))×(*Prunus persica* var. *nucipersica*×(*Prunus salicina*×*Prunus persica*))] is of large size, vigorous, upright growth and a productive and regular bearer of large size, white flesh, freestone fruit that have a unique maroon-red skin color. The fruit is further characterized by having a unique, excellent flavor with the desirable blend between a sweet, mild, sub-acid nectarine and the slight tanginess of the plum, leaving a lingering after taste of excellent eating quality. The color of the new leaves in the spring is a unique maroon-red, which fades to a near normal green color as the leaves mature during the hot summer weather. The very newest growth retains maroon pigment on the shaded, lower surface and midrib of the leaf during most of the season.

Pigment varies primarily with the high temperature during the summer.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, 5 years of age, its flowers, foliage and fruit as based on observations of specimens grown near Modesto, Calif., with color in accordance with Munsell Book of Color.

Tree:

*Size.*—Large. Pruned to 3 to 3.5 meters in height at maturity for economical harvesting of fruit.

*Vigor.*—Vigorous. Growth of 1.5 to 2 meters the first growing season.

*Form.*—Upright. Usually pruned to vase shape.

*Branching habit.*—Upright.

*Productivity.*—Productive. Usually sets 1 1/2 or more times the fruit than desired, thinning and spacing necessary to develop market size fruit.

*Bearer.*—Regular. Has had adequate fruit set 4 consecutive years. No alternate bearing observed.

*Fertility.*—Self-fertile, abundant pollen.

*Density.*—Medium dense. Pruned to vase shape by removing branches from center of tree to increase sunlight to keep fruit wood healthy.

*Hardiness.*—Hardy in all stone fruit growing areas of California. Winter chilling requirement of approximately 700 hours at or below 45° F.

Trunk:

*Size.*—Medium, stocky. Average circumference 32.38 cm at 25.4 cm above ground on a 5 year old tree.

*Texture.*—Medium shaggy, becoming rougher with age.

*Color.*—10YR 4/2 to 10YR 6/2. Color darkens with age.

Branches:

*Size.*—Medium, slender. Average circumference 9.65 cm at 1.2 meters above the ground. Crotch angle approximately 27°. Crotch angle increases with heavy fruit set.

*Surface texture.*—Smooth on new growth, varies to medium rough with age.

*Lenticels.*—Average number of 51 in a 25.8 square cm section. Average length 2.6 mm. Average width 0.6 mm. Color 5YR 4/6 to 5YR 4/8, becomes darker with age.

*Color.*—New growth 2.5R 3/8 in sun areas, 2.5GY 6/6 to 2.5GY 7/6 in the shaded areas. Old growth 7.5R 5/2.

Leaves:

*Size.*—Large. Average length 123.1 mm. Average width 37.2 mm.

*Form.*—Lanceolate.

*Apex.*—Acuminate.

*Base.*—Cuneate.

*Margin.*—Serrate.

*Thickness.*—Medium.

*Surface texture.*—Upper surface relatively smooth, slight indentation over midrib and leaf veins, glabrous. Lower surface relatively smooth, small ridges created by midrib and pinnate venation, glabrous.

*Petiole.*—Average length 7.7 mm. Average width 1.3 mm. Longitudinally grooved. Glabrous. Color — new petiole, in sun 7.5R 2/8 . Older petiole in shade 2.5GY 6/6.

*Glands.*—Medium size. Average length 1.1 mm. Average width 0.7 mm. Number varies from 1 to 4, average number 2. Located on base of leaf blade and the upper portion of the petiole. Color — Upper surface rim 7.5R 4/10. Lower vertical surface 2.5GY 6/6 to 2.5GY 6/8.

*Color.*—New leaves — upper surface 7.5R 2/4. Lower surface 7.5R 2/6. Old leaves — upper surface 5GY 4/6. Lower surface 7.5GY 5/4.

*Midvein color.*—On new leaves 5R 3/4 to 5R 4/4, on older leaves 2.5GY 8/6.

Flower buds:

*Size.*—Large. Average length 16.3 mm. Average diameter 11.2 mm.

*Hardiness.*—Hardy in all stone fruit growing areas of California.

*Form.*—Plump, obtuse.

*Pedicel.*—Average length 3.5 mm. Average width 2.3 mm. Color 2.5GY 8/8.

*Color.*—5RP 7/8.

Flowers:

*Size.*—Large, showy. Average height 19.5 mm. Average diameter 44.0 mm.

*Petals.*—Number 5, alternately arranged to sepals. Shape — orbicular. Average length 19.3 mm. Average width 19.5 mm. Margin varies from entire to sinuate. Color 2.5RP 8/6.

*Sepals.*—Number 5, alternately arranged to petals. Shape — ovate, apex rounded. Pubescence — inner surface glabrous, outer surface pubescent. Average length 6.3 mm. Average width 5.0 mm. Color — upper surface 7.5RP 5/10 on tips and 2.5GY 8/6 on base. Lower surface 7.5RP 3/10.

*Stamens.*—Average number per flower 47. Average filament length 12.5 mm. Filament color N/9.5 when flower first opens, becoming 5RP 4/12 as flower ages. Anther color 10RP 4/12.

*Pollen.*—Present, self fertile. Color — 2.5Y 8.5/8.

*Pistil.*—Normally 1, varies from 1 to 2. Average length 19.1 mm. Surface is glabrous. Color 7.5RP 5/10. Stigma approximately 3.2 mm higher than anthers.

*Fragrance.*—Very slight.

*Blooming period.*—Date of First Bloom Feb. 21, 2001. Date of Petal Fall Mar. 6, 2001. Varies slightly with climatic conditions.

*Color.*—2.5RP 8/6.

*Number flowers per flower bud.*—One.

*Pedicel.*—Average length 4.1 mm. Average width 2.3 mm. Color 5GY 7/4.

Fruit:

*Maturity when described.*—Firm ripe.

*Date of first picking.*—Jul. 9, 2001.

*Date of last picking.*—Jul. 16, 2001. Varies slightly with climatic conditions.

*Size*.—Large. Average diameter axially 63.5 mm. Average transversely in suture plane 70.2 mm. Average weight 190.28 grams, varies slightly with fertility of the soil, amount of thinning and climatic conditions.
*Form*.—Nearly globose, some fruit with slight pistil point.
*Suture*.—Nearly smooth, extends from base to apex.
*Ventral surface*.—Nearly rounded. Only slightly lipped.
*Apex*.—Usually rounded, varies from rounded to slight pistil point.
*Base*.—Retuse.
*Cavity*.—Rounded to slightly elongated in suture plane. Average depth 7.1 mm. Average diameter 10.3 mm.

Stem:
*Size*.—Average length 6.1 mm. Average diameter 2.3 mm.
*Color*: 5GY 6/6.

Flesh:
*Ripens*.—Evenly.
*Texture*.—Firm, meaty.
*Fibers*.—Few, small, tender.
*Firmness*.—Firm, comparable to 'Royal Gold' Peach (U.S. Plant Pat. No. 2,663).
*Aroma*.—Slight.
*Amydgalin*.—Undetected.
*Eating quality*.—Excellent.
*Flavor*.—Excellent, a good balance between sugar and acid.
*Juice*.—Moderate amount, enhances flavor.
*Brix*.—13.6°. Varies slightly with amount of fruit per tree and climatic conditions.
*Color*.—10Y9/1. Pit cavity — 5R 3/10. Very slight bleeding of red around pit cavity into the flesh.

Skin:
*Thickness*.—Medium.
*Surface*.—Smooth.
*Down*.—Wanting.
*Tendency to crack*.—None.
*Color*.—Ground color 10YR 9/1. Nearly overspread with 5R 3/8 to 7.5R 3/8. Some small areas primarily on base of fruit, showing ground color, leaving a random mottled pattern.
*Tenacity*.—Tenacious to flesh.
*Astringency*.—None.

Stone:
*Type*.—Freestone.
*Size*.—Large. Average length 32.5 mm. Average width 24.9 mm. Average thickness 17.2 mm.
*Form*.—Obovate.
*Base*.—Varies from straight to rounded.
*Apex*.—Cuspidate. Average length 1.7 mm.
*Surface*.—Irregularly furrowed toward the apex, pitted toward base. Pits vary from round to elongated. Usually one deep furrow on each side of suture.
*Sides*.—Vary from equal to unequal, with one side extending further from the suture plane.
*Ridges*.—Medium width, relatively smooth.
*Tendency to split*.—Very slight.
*Color*.—5YR 3/6 to 5YR 4/6, when dry and clean of flesh.

Kernal:
*Form*.—Elliptic.
*Taste*.—Bland.
*Viability*.—Viable, complete.
*Size*.—Average length 17.6 mm. Average width 10.9 mm. Average thickness 4.1 mm.
*Skin*.—Color 5YR 4/8 when dry.

Use: Dessert. Market — local and long distance.

Keeping quality: Good, held firm in cold storage 3 weeks at 38°0 to 42° F. with minimal loss of flavor, firmness or internal flesh breakdown.

Shipping quality: Good, minimal scarring of skin or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of interspecific tree, substantially as illustrated and described, characterized by its large size, vigorous, upright growth and being a productive and regular bearer of large size, white flesh, freestone fruit that have a unique maroon-red skin color and a unique flavor that is a blend between a mild, sweet, sub-acid nectarine and the tanginess of a plum; the tree is further characterized with unique maroon-red color of the new leaves, which fades to near normal green with maturity and hot summer weather.

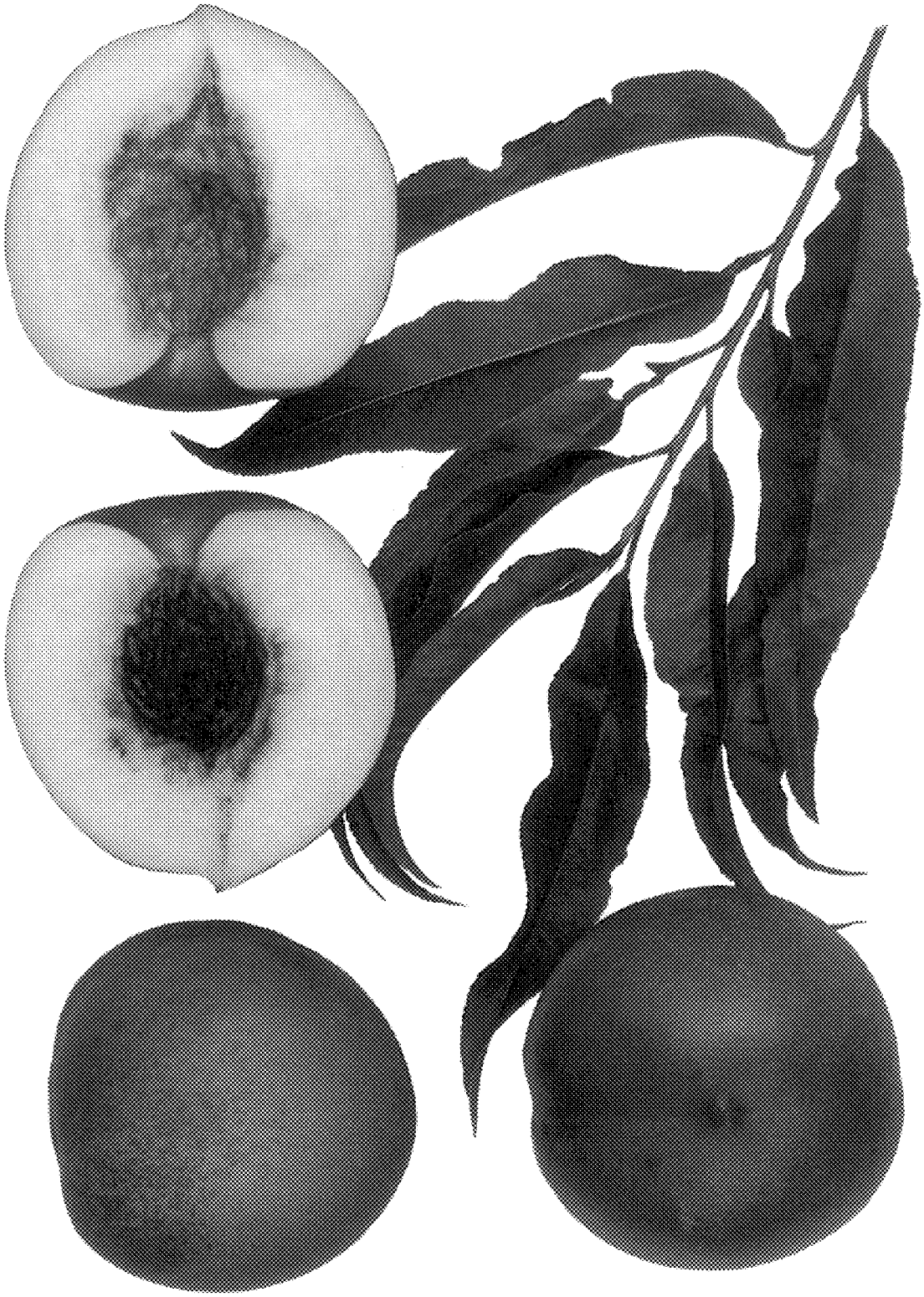

* * * * *